United States Patent
Friend et al.

(10) Patent No.: US 7,410,474 B1
(45) Date of Patent: Aug. 12, 2008

(54) METHODS AND MEANS FOR EXTRACORPOREAL ORGAN PERFUSION

(75) Inventors: Peter Friend, Oxford (GB); Andrew Butler, Cambridgeshire (GB); Michael Rees, Toledo, OH (US)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 09/958,681

(22) PCT Filed: Apr. 12, 2000

(86) PCT No.: PCT/GB00/01271

§ 371 (c)(1),
(2), (4) Date: Feb. 21, 2002

(87) PCT Pub. No.: WO00/60936

PCT Pub. Date: Oct. 19, 2000

(30) Foreign Application Priority Data

Apr. 12, 1999 (GB) .................................. 9908335.4

(51) Int. Cl.
*A61M 37/00* (2006.01)
*A01N 1/02* (2006.01)
*A61N 1/30* (2006.01)

(52) U.S. Cl. ............................ 604/6.11; 604/8; 604/19; 435/284.1

(58) Field of Classification Search ................ 604/4.01, 604/5.01, 6.09, 6.11, 6.15, 6.16, 7–10, 6.13, 604/6.14, 65–67; 435/284.1, 1.1, 1.2, 286.6, 435/286.5; 210/600, 645; 422/44–46
See application file for complete search history.

(56) References Cited

U.S. PATENT DOCUMENTS

| | | | | |
|---|---|---|---|---|
| 4,666,425 A | * | 5/1987 | Fleming | ................ 604/6.07 |
| 5,494,822 A | * | 2/1996 | Sadri | ................ 435/284.1 |
| 5,786,136 A | * | 7/1998 | Mayer | ................ 435/1.2 |
| 5,807,737 A | | 9/1998 | Schill et al. | |
| 6,100,082 A | * | 8/2000 | Hassanein | ................ 435/284.1 |
| 6,331,658 B1 | * | 12/2001 | Cooper et al. | ................ 800/14 |
| 6,642,045 B1 | * | 11/2003 | Brasile | ................ 435/284.1 |

FOREIGN PATENT DOCUMENTS

| | | |
|---|---|---|
| EP | 0376763 | 7/1990 |
| WO | 9915011 | 4/1999 |

* cited by examiner

*Primary Examiner*—Leslie R Deak
(74) *Attorney, Agent, or Firm*—Nixon & Vanderhye P.C.

(57) ABSTRACT

Apparatus and methods of operation of apparatus for the extracorporeal perfusion of organs are provided which support viability and function of an organ such as a liver, generally outside the body. Blood is supplied as described herein to an organ such as a liver under physiological pressure but without forcing blood flow at any particular rate such that the organ is allowed to auto-regulate blood flow. This allows for organ preservation or resuscitation prior to transplantation, maintenance of organs for use in experimental study of isolated liver physiology, and treatment of patients suffering from organ failure.

22 Claims, 10 Drawing Sheets

Figure 2
Haemodynamic Function
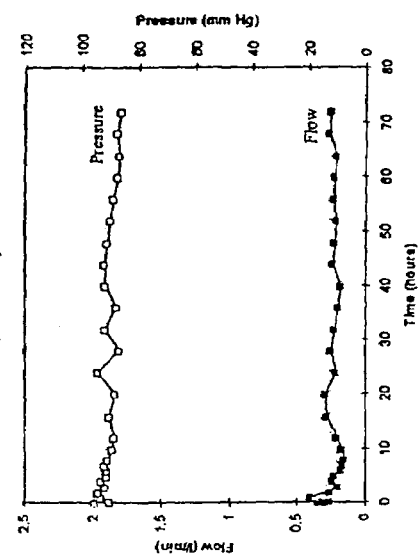
Figure 2c. Hepatic Artery Pressure and Flow
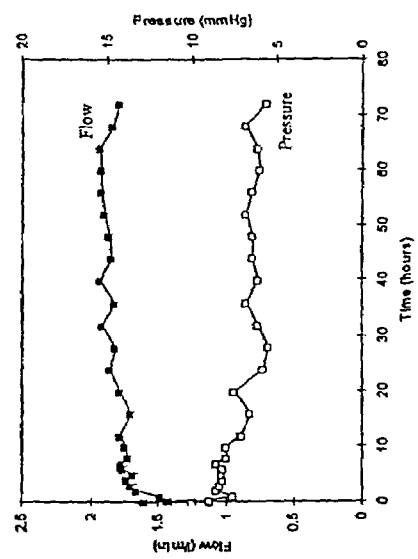
Figure 2b. Portal Pressure and Flow
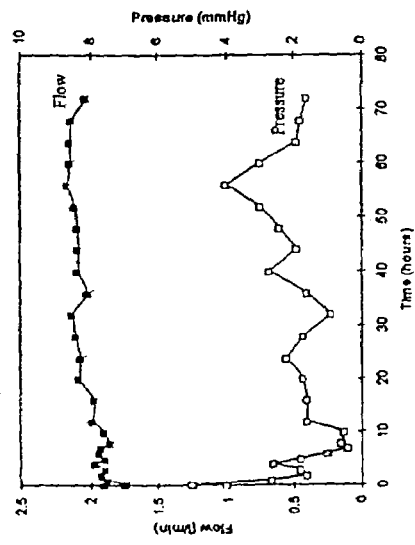
Figure 2a. IVC Pressure and Flow

Metabolic Function
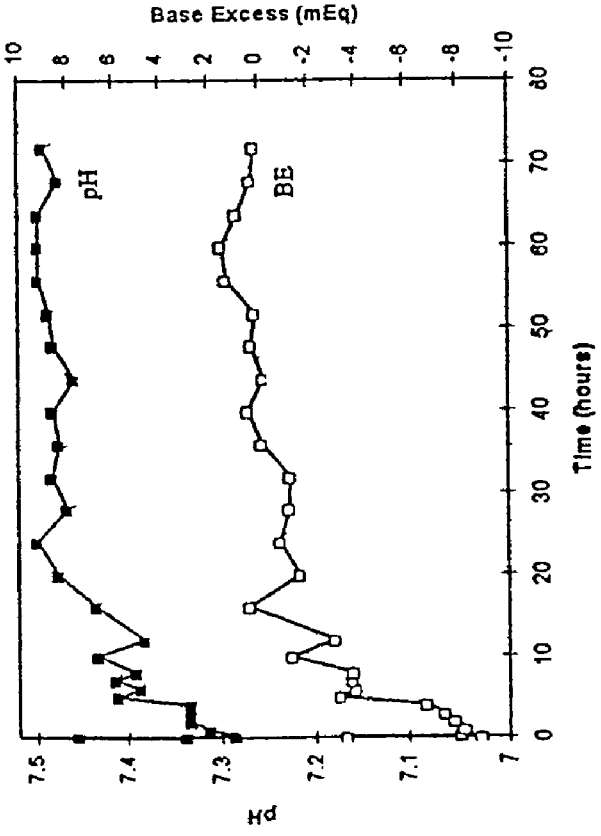
Figure 3b. Potassium and Ionized Calcium
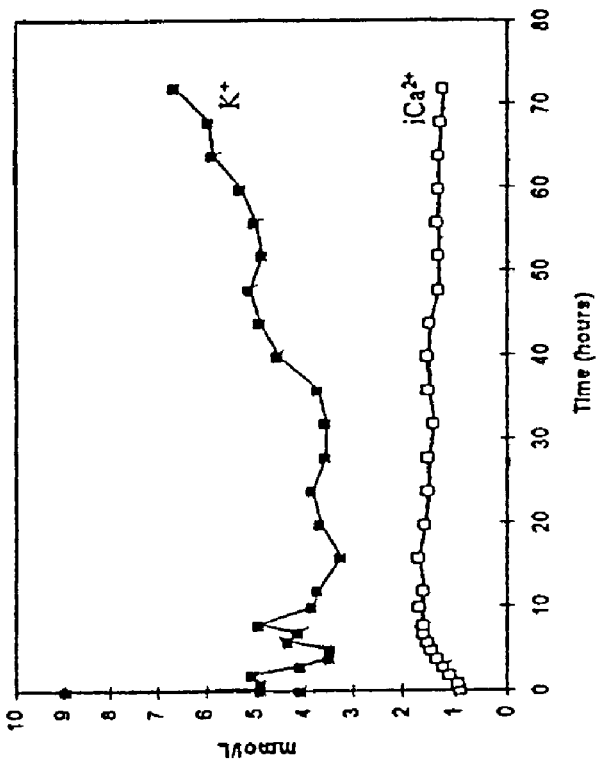
Figure 3a. pH and Base Excess
Figure 3

Figure 4
Synthetic Function
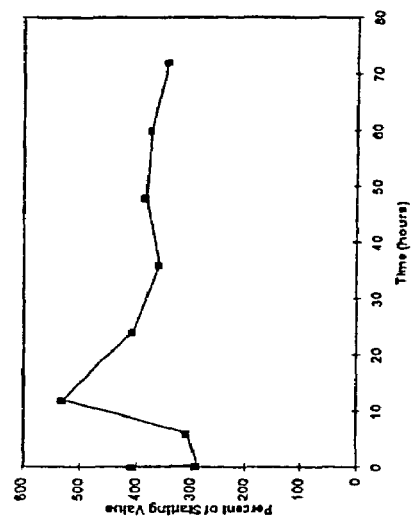
Figure 4a. Urea and Creatinine
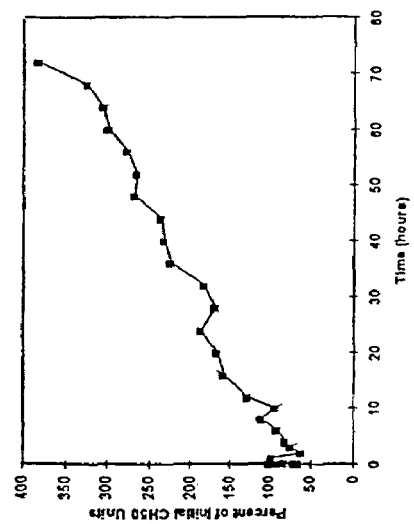
Figure 4b. Complement Activity
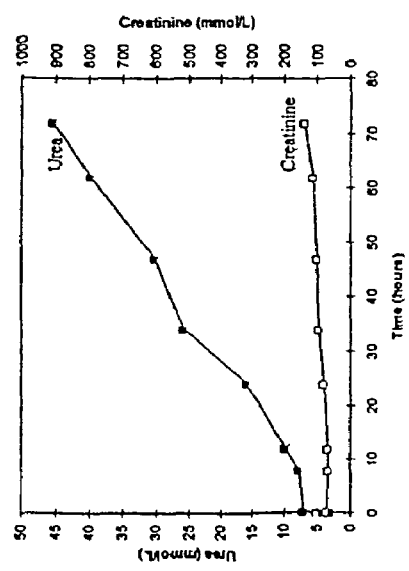
Figure 4c. Factor V Activity Figure 5 Liver Enzymes, Bile Production, and Oxygen Consumption
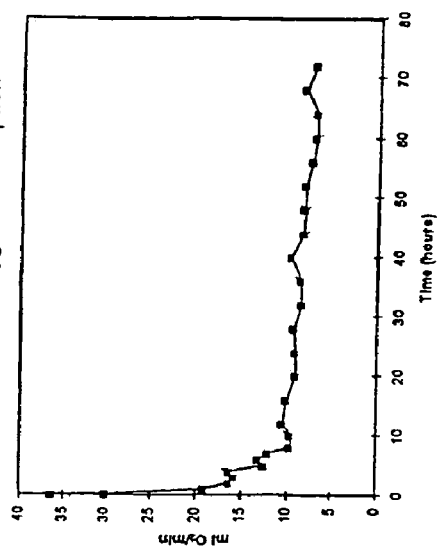
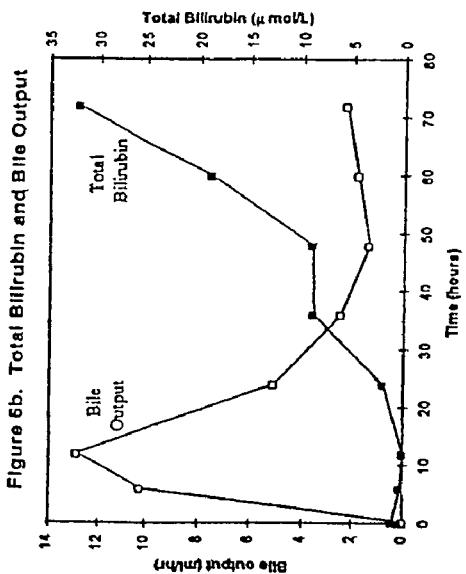
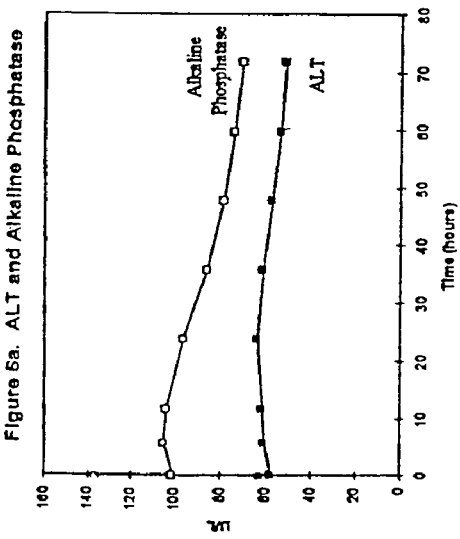

Metabolic Function
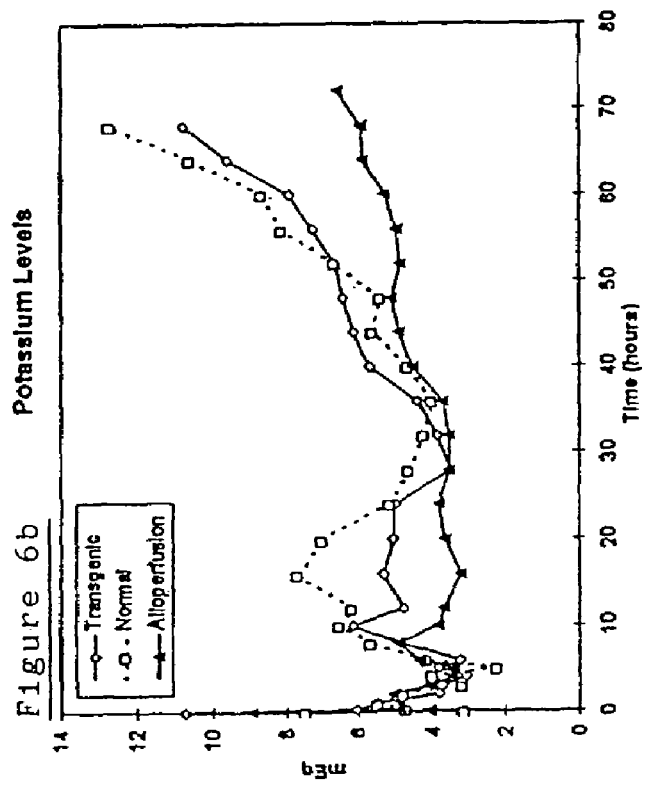
Figure 6a
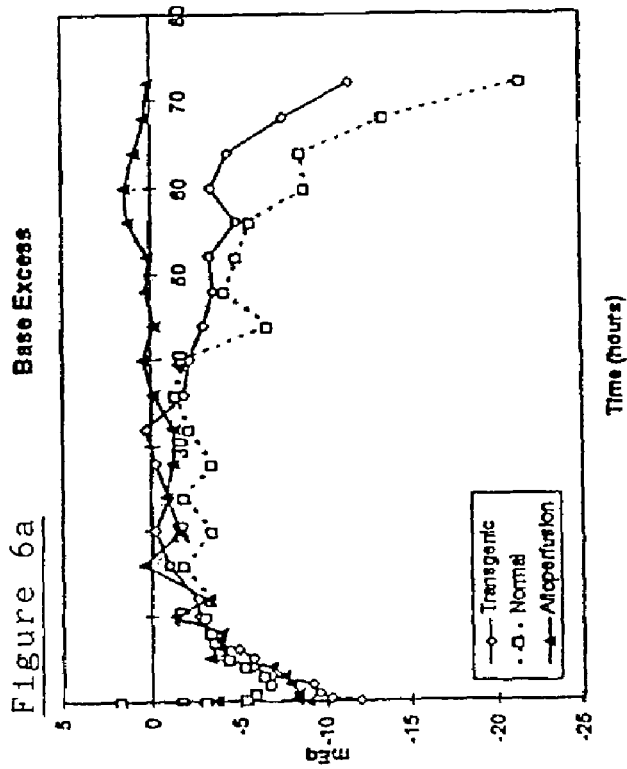
Figure 6b
Figure 6

Total Bilirubin and Bile Production

Platelets, White Blood Cells, and Hematocrit
Figure 8
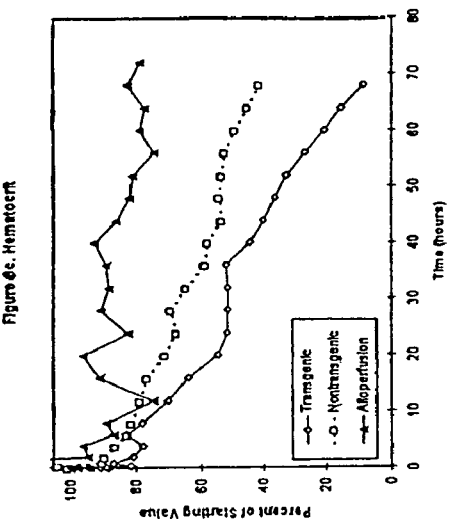
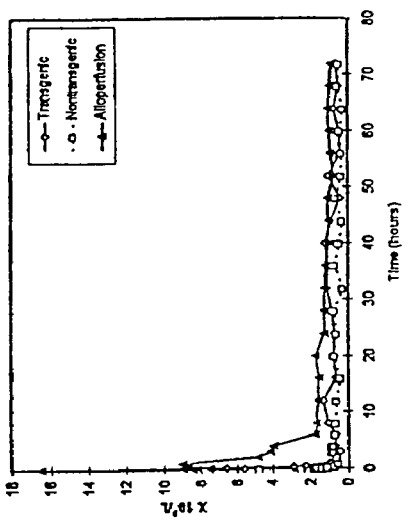
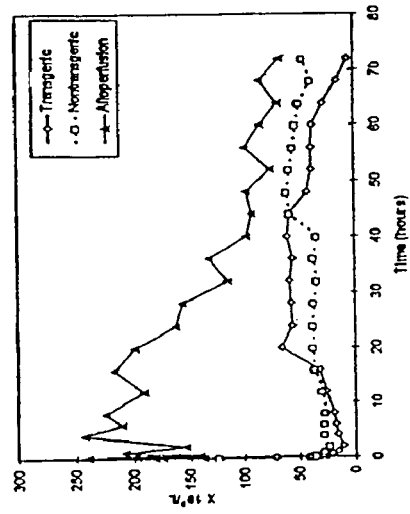

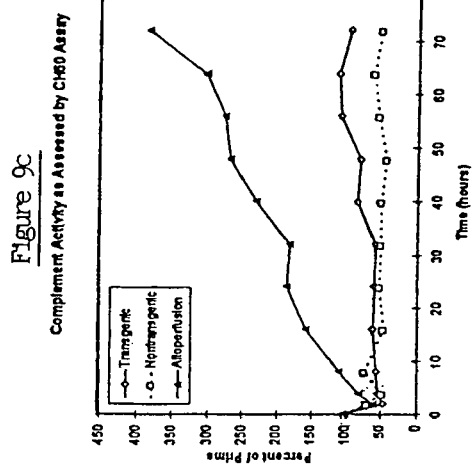
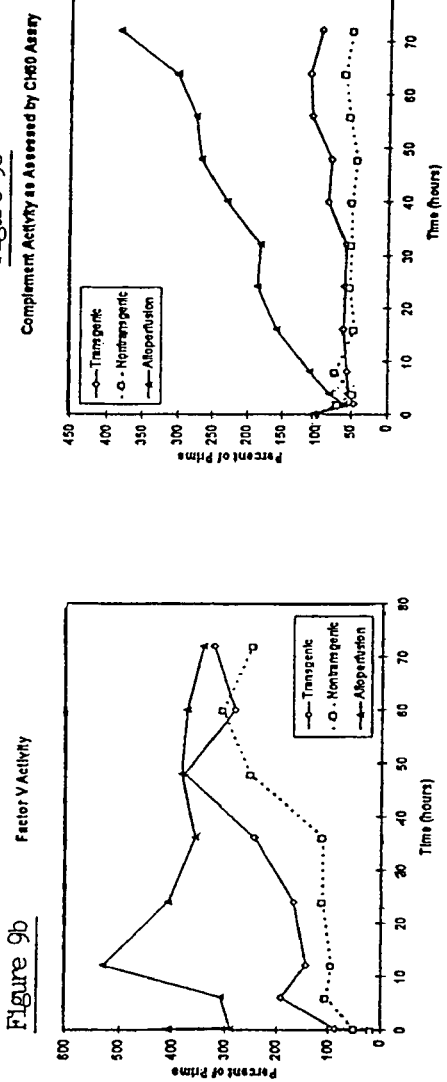
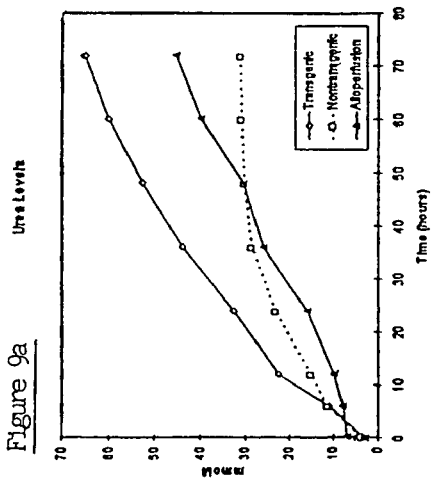
Figure 9
Figure 9a • Figure 9b • Figure 9c
Synthetic Function

METHODS AND MEANS FOR EXTRACORPOREAL ORGAN PERFUSION

The present application is a 371 U.S. National Phase of PCT/GB00/01271, filed 5 Apr. 2000, which claims benefit of GB9908335.4 filed 12 Apr. 1999.

The present invention relates to perfusion of organs, in particular the extracorporeal perfusion of organs, whether human or non-human, e.g. porcine, and whether non-transgenic or transgenic. Apparatus and methods of operation of such apparatus are provided for perfusion to support viability and function of an organ such as a liver, generally outside the body. This allows for organ preservation or resuscitation prior to transplantation, for instance while a transplant recipient is prepared, maintenance of organs for use in experimental study of isolated liver physiology, and treatment of patients suffering from organ failure.

The invention is based on the inventors' unexpected findings relating to autoregulation of blood flow within an organ. Advantageously, in accordance with the present invention blood is provided to an organ such as a liver under physiological pressure but without forcing blood flow at any particular rate. The organ is allowed to autoregulate blood flow. (Any surplus blood flow may be allowed to run off.) Also advantageously, outflow pressure from a perfused organ (vena cava in a liver) can be maintained. The histological appearances of livers perfused using the invention are within normal limits even after 72 hours. This represents a significant advance over known techniques, problems with which date back a long time.

Isolated liver perfusion has been studied for over 90 years (Bernard C., C.R. Acad. Sci. 1855; 41: 461). However, most experimental isolated liver perfusion work has been carried out with non-blood solutions in rodent models in order to assess various aspects of hepatic function (Gores et al., Hepatology, 1986; 6: 511-7). Clinical application of ex vivo liver perfusion as a means of supporting patients with acute. liver failure was studied extensively in the late 1960s and early 1970s (Eiseman et al., Annals of Surgery, 1965, 329-345; Eiseman, Ann. Roy. Coll. Surg. Engl. 1965; 38: 329-349; Watts et al., British Medical Journal, 1967; 341-345; Abouna, The Lancet, 1968, 1216-1218; Abouna et al., Brit. J. Surg., 1969; 56: 223-225; Condon et al., The American Journal of Surgery, 1970; 119: 147-154; Abouna et al., The Lancet, 1970; 391-396; Lempinen et al., Scandinavian Journal of Gastroenterology, 1971; 6: 377-383; Chalstrey et al., British Journal of Surgery, 1971; 58: 522-524; Hickman et al., Scand. J. Gastroent., 1971; 6: 563-568; Parbhoo et al., The Lancet, 1971; 659-665; Abouna et al., Surgery, 1972; 71: 537-546; Abouna et al., Surgery Obstetrics and Gynaecology, 1973; 137: 741-752; Abouna et al., Transplantation, 1974; 18: 395-408). However this technique fell into abeyance between the end of the 1970s and the early 1990s, because of the advent of other treatments, particularly successful liver transplantation.

More recently, there has been a resurgence of interest in extracorporeal liver perfusion (Fair et al., AASLD, 1993 A899; Fox et al., The American Journal of Gastroenterology, 1993; 88: 1876-1881; Chari et al., NEJM, 1994; 331: 234-237). This has resulted from improvements in cardiopulmonary bypass technology, which have also led to successful extracorporeal membrane oxygenation, and developments in genetic engineering, which have resulted in the production of transgenic pigs resistant to hyperacute rejection (Cozzi et al., Nature Medicine, 1995; 1: 964-966). Genetic modification of the regulation of complement activation has abrogated the immediate immunological reaction between previously discordant species.

Whilst the use of organs from concordant species has major immunological advantages, there are major practical restrictions. The availability of human livers is limited and those available must be used for clinical transplantation. The use of organs from non-human primates poses significant problems, although organs from baboons have been successfully employed. Major concerns exist in relation to primate zoonoses; also, the majority of non-human primates do not attain the necessary size to be effective in human organ replacement.

It is known that the critical effector mechanism in hyperacute rejection between discordant species is activation of the complement cascade (Platt et al.: Role of Natural Antibody-Antigen Interactions in Xenotransplantation. In: Xenotransplantation. Cooper et al., eds. Berlin: Springer, 1997; 17-23). Complement activation is normally suppressed by the presence of species-specific cell surface proteins, regulators of complement activity (Liszewski et al., Adv. Immunol. 1996; 61: 201-283). Recently a colony of pigs transgenic for one such regulator, human decay accelerating factor (hDAF) has been produced (Cozzi and White, Nat-Med. 1995; 1: 964-966). There is evidence that hearts and kidneys from these animals, transplanted into primates, are not hyperacutely rejected and behave as though from a concordant species (Schmoeckel et al., Transplant. Proc. 1997; 29: 3157-3158). Transgenic pigs therefore provide a source of "concordant" organs.

These factors have stimulated several groups to re-explore the possibility of supporting patients in hepatic failure with extracorporeal porcine livers. The success of organ transplantation has also stimulated interest in using extracorporeal perfusion as a means of organ preservation and resuscitation of organs from marginal donors (Schon et al., 8th Congress of the European Society for Organ Transplantation, 1997, Abstract TRP4).

A major limitation of previous studies has been the short duration of perfusion, no more than 24 hours (Neuhaus et al., Int. J. Artif. Organs, 1993; 16: 729-739).

In one aspect, the present invention provides mammalian organ perfusion apparatus which on connection to input artery and output vein of a mammalian organ provides a fluid circuit for flow of blood through the organ, in which circuit there is, preferably in the following order, an output channel for connection to the output vein of the organ, an outflow pump of adjustable speed for maintaining physiological pressure in the output vein of the organ, an oxygenator and a heat exchanger, and an input channel for connection to an input artery of the organ, the circuit further comprising a device for maintaining physiological pressure and variable flow in the input artery of the organ while allowing the organ to autoregulate blood flow through itself to achieve physiological arterial flow.

In a further aspect, where the organ is a liver, the present invention provides mammalian liver perfusion apparatus which on connection to vena cava, hepatic artery and portal vein of a mammalian liver provides a fluid circuit for flow of blood through the liver, in which circuit there is, preferably in the following order, an output channel for connection to the vena cava, an outflow pump of adjustable speed for maintaining physiological pressure in the vena cava, an oxygenator and a heat exchanger, and a bifurcating channel dividing the circuit to input channels for connection to the hepatic artery and portal vein, the circuit further comprising a device for maintaining physiological pressure in the hepatic artery and physiological flow in the portal vein while allowing a liver when connected to the apparatus to autoregulate blood flow through the artery and to autoregulate pressure in the portal vein.

Such apparatus provides a circuit for blood flow. An individual may be joined to the circuit, preferably a human. The individual's circulation may be connected to the circuit via cannulae placed in large veins (positioned by open surgery or percutaneously). Outflow from the individual is returned to the perfusion circuit at a point preceding the organ. Inflow to the individual is of blood that has passed through the organ and is oxygenated. By way of example with reference to the perfusion apparatus circuit shown in FIG. 1, connection to a patient may be at a point after the gate clamp indicated in the spur shown in the figures as leading to the reservoir, with the return from the patient leading to the reservoir. As noted, extracorporeal organ support of humans has been practised for many years, and techniques for and precautions to be taken when connecting patients to extracorporeal perfusion apparatus are well known to those skilled in the art. For instance it is standard to supply prostacyclin and heparin, and to allow bile to drain from a liver. A circuit may additionally include one or more flow meters and one or more pressure meters.

Whereas previously extra-corporeal perfusion or organs such as livers has relied upon an arbitrary selection of either flow or pressure (in the portal vein for a liver), these have not been varied independently.

The present invention allows for maintenance of physiological levels of both flow and pressure. The inventors have observed that in the liver portal pressure is directly related to inferior vena caval pressure and that portal flow (rather than pressure) is directly related to pressure applied from the portal venous reservoir (in preferred embodiments the height of portal venous reservoir above the liver, where blood is supplied from there by gravity). The liver responds to increased portal pressure by reduction in portal vascular resistance, maintaining constant portal pressure.

In the circuit of the invention, the outflow from the organ is pumped so that physiological pressure is maintained, e.g. by varying pump speed, in the relevant vein, which for the liver is the vena cava. Physiological inflow may be achieved by adjustment of pressure of the supply, e.g. portal vein for the liver. In a preferred embodiment of the present invention physiological portal flow is achieved by adjustment of the height of the portal reservoir above the liver. The present invention allows for establishment of normal levels of not only portal pressure but also portal flow. The arterial inflow to a liver perfused in accordance with the invention may be set at a physiological pressure, the flow rate bing determined by the vascular resistance of the liver. The general principle of the invention as applicable to a variety of organs is to set the pressure of inflow at a physiological level, with a variable flow rate depending on vascular resistance of the organ, allowing for physiological autoregulation to occur.

The circuit employed in aspects of the invention as exemplified with respect to the liver further comprises a device for maintaining physiological pressure in the hepatic artery and physiological flow in the portal vein while allowing a liver when connected to the apparatus to autoregulate blood flow through the artery and to autoregulate pressure in the portal vein. Such a device may include a reservoir for collection of run-off blood resulting from autoregulation by the liver of flow in the hepatic artery, and such a reservoir may be for supply of blood to the input channel for connection to the portal vein of a liver. Supply of blood to the portal vein of a liver when connected to the apparatus may be from the reservoir under force of gravity.

Conveniently, inflow pressure can be adjusted while allowing for autoregulation of inflow rate by providing a bifurcating tube allowing for run-off from the connection to the input blood vessel. The resistance of the run-off spur of the bifurcation may be altered by means of partial occlusion, e.g. by clamping, for adjustment of pressure in the input to the organ. Autoregulation of flow by the organ leads to run-off of blood to the reservoir. Alternative ways of achieving the same result include an automated controller that fixes the pressure within predetermined parameters yet allows for variable flow in response to autoregulation by the organ. In the case of a liver, such a system may employ two pumps, one to provide hepatic arterial flow at constant pressure/variable flow, and one to fill the portal venouse reservoir at low pressure.

In a further aspect, the present invention provides a method of operating an organ perfusion apparatus. The apparatus may have the components identified herein. One embodiment of a method according to this aspect of the invention as applied to a liver may be a method operating mammalian liver perfusion apparatus connected to vena cava, hepatic artery and portal vein of a mammalian liver wherein the apparatus provides a fluid circuit for flow of blood through the liver, the method including adjusting the rate of outflow pumping to maintain physiological pressure in the vena cava, adjusting pressure of supply to the input channel connected to the hepatic artery to maintain physiological pressure in the hepatic artery and physiological flow in the portal vein, and allowing the liver to autoregulate blood flow through the artery and to autoregulate pressure in the portal vein.

A further aspect provides a method of perfusing a mammalian organ extracorporeally, which method includes pumping arterial blood inflow to the organ to maintain physiological pressure and variable flow in the artery of the organ and pumping venous outflow from the organ to maintain physiological pressure in the output vein of the organ, while allowing the organ to autoregulate blood flow through itself to achieve physiological arterial flow.

Where the organ is a liver, a method according to the invention may include adjusting portal vein flow and pumping blood outflow from the liver to maintain physiological pressure in the vena cava of the liver, while allowing the liver to autoregulate portal pressure.

A further aspect of the invention provides a method of maintaining viability of a mammalian organ, in which method the organ is perfused in accordance a method as disclosed herein. Perfusion in accordance with the present invention allows for maintenance of viability of an organ such as a liver for at least about 72 hours, preferably at least about 96 hours, more preferably at least about 120 hours.

The experimental exemplification of embodiments of the present invention included below relates to perfusion of livers. In the light of the inventors' findings, it is scientifically reasonable to assume that the apparatus and methods of the invention are effective when applied to other organs, such as kidneys, pancreas or small bowel. Perfusion of an organ with a single inflow (such as a kidney) will involve a modified circuit with the reservoir feeding back into the inflow of the pump. Excess blood flow may be provided at a fixed pressure to the artery of the organ while providing a means of egress for any blood flow that is in excess to that required by the organ. Alternatively, arterial flow may be provided by a pump at a variable rate with fixed arterial pressure.

An organ perfused in accordance with the present invention may be human or non-human, and may be non-transgenic or transgenic. Non-human organs may be modified in order to increase compatibility with connection to a human and/or perfusion with human blood. An example of a modification that successfully used to increase concordance of non-human, especially porcine organs, is transgenic modification such that the organs express the human complement component Decay Accelerating Factor (hDAF) (see e.g. Cozzi and White, and Schmoeckel et al. supra).

Blood used in the perfusion may be human or non-human, e.g. porcine for a porcine organ, and this may depend on the purpose of the perfusion.

A human organ will generally be perfused with human blood. Where the organ is to be connected to a human subject, the blood will be human and needs to be antigenically compatible with respect to ABO. A non-human, e.g. pig organ, may be perfused with the relevant non-human blood (e.g. pig), or human blood for instance when the organ is modified in the manner described above (e.g. transgenic for hDAF).

Preferably the blood is citrated. The inventors have found the function of livers perfused with citrated blood to be markedly superior to those perfused with heparinised blood. Citrate is an important metabolic substrate of the liver.

In a liver perfusion circuit according to the invention, preferably fluid that leaks from the organ, including ascites, is recirculated back to the liver, preferably via the portal vein or, if not, via the hepatic artery. This has the advantage of maintaining vascular volume, and also retaining plasma proteins which would probably be lost if the ascites was replaced with colloid/crystalloid solutions.

Apparatus according to the invention may include a channel for collection of fluid that leaks from the organ and its transport to the input blood reservoir.

Preferably perfusion is "warm perfusion", i.e. at physiological temperature, generally 37° C. for a human organ and 39° C. for a pig organ.

Preferably a liver for use in the present invention is preserved with hypertonic citrate, rather than the current standard liver transplant preservation solution (University of Wisconsin) which is based on lactobionate. Preservation solution is washed out of the liver immediately before perfusion starts.

A further advantage of a perfusion circuit according to the present invention arises from the fact that when such a circuit is connected to a patient, the circulation of the patient is connected to the reservoir of the circuit and the rate of patient perfusion can therefore be different from that of the extracorporeal organ perfusion.

The inventors have also found that perfusion of a porcine liver, whether normal or genetically modified, with human blood leads to extraction of human red blood cells by Kupffer cells of the liver. For the purpose of clinical application, blocking of this Kupffer cell function, e.g. by ablation of the cells, allows for long-term perfusion without excessive red blood cell consumption. Kupffer cell function may be blocked/ablated by treatment of the donor animal prior to removal of the organ or by treatment of the organ with clodrinate or gadolinium, or immunoglobulin or immunoglobulin/complement lysis, or using any suitable technology available to those skilled in the art.

Accordingly a further aspect of the present invention provides a method of reducing red blood cell consumption by a non-human organ on perfusion with human blood, the method comprising application to the organ of a treatment to block or ablate Kupffer cell function prior to exposure of the organ to the human circulation or perfusion with human blood, whether a perfusion technique in accordance with other aspects of the present invention is employed or any other perfusion technique available to the skilled person.

Further aspects and embodiments of the present invention will be apparent to those skilled in the art in view of the following experimental exemplification with reference to the figures.

BRIEF DESCRIPTION OF THE FIGURES

FIG. 2 shows haemodynamic parameters during extracorporeal liver perfusion as described in Example 1 below:

FIG. 2a shows total flow as measure exiting the liver via the inferior vena cava, and IVC pressure measured at confluence of hepatic veins.

FIG. 2b shows portal flow as measured entering the liver via the portal vein, and portal pressure measured by monitoring line in portal veing.

FIG. 2c shows hepatic artery flow calculated as difference between total and portal flow, and hepatic artery pressure measured as direct arterial line pressure.

FIG. 3 show metabolic parameters during extracorporeal liver perfusion as described in Example 1 as measured by arterial blood gas analysis (CIBA Corning, 288 Blood Gas System).

FIG. 3a shows normal reference range pH 7.35 to 7.45, and Base Excess −2 to 2 mEq.

FIG. 3b shows normal reference range potassium 3.5 to 4.6 mmol/L, and ionized calcium 1.13 to 1.3 mmol/L.

FIG. 4 shows markers of synthetic function during extracorporeal liver perfusion.

FIG. 4a shows urea levels versus creatinine levels expressed on clinically relevant y-axis scales.

FIG. 4b shows complement activity as measured by $CH_{50}$ analysis using sheep RBC. Data are expressed as a percent of the $CH_{50}$ units of the plasma just prior to perfusing the liver.

FIG. 4c shows factor V levels measured by replacing factor V deficient human blood and expressed as a percent of normal human factor V levels.

FIG. 5 shows markers of liver injury and function during extracorporeal liver perfusion.

FIG. 5a shows ALT (SGPT) levels (normal human range up to 50 U) and alkaline phosphatase levels (normal human range 30-135 U).

FIG. 5b shows bile output measured as ml bile produced per hour and total bilirubin expressed in μmol/L (normal human range up to 17 μmol/L).

FIG. 5c shows oxygen consumption calculated by the Fick equation and expressed as ml $O_2$/min/liver.

FIG. 6 shows metabolic parameters during extracorporeal liver perfusion as described in Example 2 as measured by arterial blood gas analysis.

FIG. 6a shows normal human reference range for base excess is −2.5 to 2.5 mEq.

FIG. 6b shows normal human reference range for potassium is 3.5 to 4.6 mmol/L.

FIG. 7a shows hDAF transgenic porcine liver perfused with human blood.

FIG. 7b shows nontransgenic porcine liver perfused with human blood.

FIG. 7c shows nontransgenic porcine liver perfused with porcine blood.

FIG. 8 shows full blood count analysis was performed using a Coulter counter (T660) adjusted for measurement of porcine blood. Transgenic represents hDAF transgenic porcine livers perfused with human blood, Nontransgenic represents wild-type porcine livers perfused with human blood and Alloperfusion represents wild-type porcine livers perfused with porcine blood.

FIG. 8a shows platelet counts, ($\times 10^9$/L)

FIG. 8b shows nucleated cell counts ($\times 10^9$/L).

FIG. 8c shows hermatocrit (expressed as a percent of the starting hematocrit of the blood prior to starting extracorporeal perfusion).

FIG. 9a shows urea measured by standard clinical laboratory technique. Transgenic vs. Normal, p=NS.

FIG. 9b shows complement activity measured using a functional assay by lysis of sheep RBC and CH50 determination. Results are expressed as percent of CH50 present prior to liver perfusion (prime blood) Transgenic vs. Normal, p=NS.

FIG. 9c shows factor V activity measured using a functional assay by reconstituting factor V deficient human serum. Results are expressed as percent of normal human serum. Transgenic vs. Normal, p=NS.

EXAMPLE 1

Extracorporeal Perfusion of Pig Livers

Blood Donor

Figure 1:
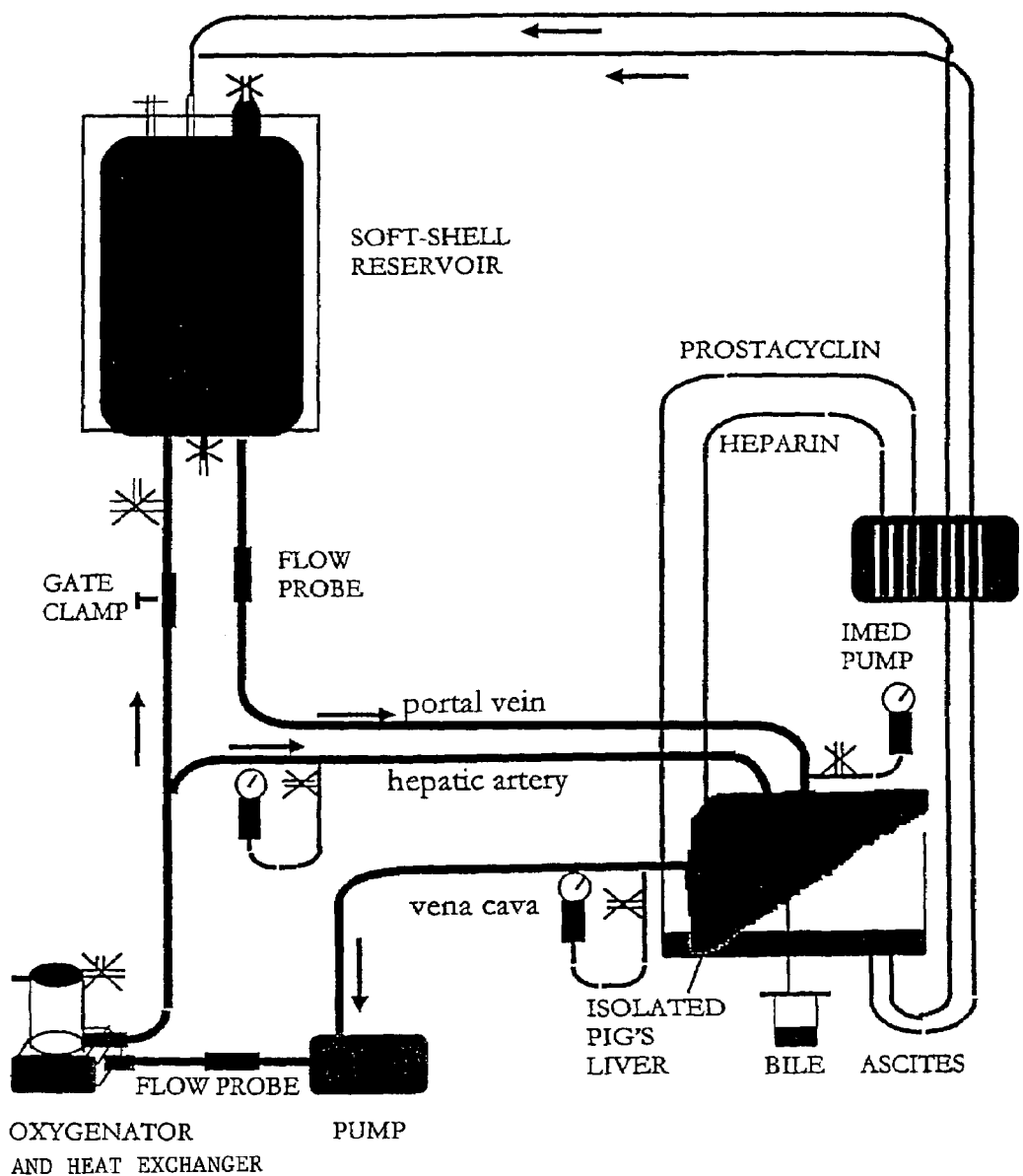
FIG. 1 outlines perfusion apparatus according to an embodiment of the invention, connected to a liver.

Large white pigs (35-70 kg) were used in these studies, five as liver donors and five as blood donors. All animals were treated in accordance with the Animal Protection Act, 1986 of the United Kingdom. Blood donor pigs were pre-medicated with 10 mg/kg ketamine (Willows Francis Veterinary, Ketaset) and 1 mg/kg midazolam (Roche, Hypnovel) IM, followed by halothane anaesthesia. The external jugular vein was cannulated, 15,000 U of heparin was given intravenously and blood was collected in citrated bags via gravity drainage until circulation ceased. Blood was used immediately or stored at 4° C. and used within one week of collection.

Liver Donor

Animals were pre-medicated as above, an ear vein cannulated and anaesthesia induced using 4 mg/kg propofol i.v. (Zeneca, Diprivan). The animal was intubated using an extended endotracheal tube. Pulse oximetry via a tail probe was used to follow oxygenation and end tidal $CO_2$ was measured. After intubation, a 14 gauge cannula was sited to allow for fluid replacement during the hepatectomy. Anaesthesia was maintained with IV propofol (10 mg/kg/hr) throughout the procedure. A midline incision was made. The bile duct was divided and the hepatic vessels identified and isolated in the standard fashion. The liver was dissected until connected to the donor only by its vascular attachments. Throughout this procedure, meticulous attention was paid to haemostasis to minimize subsequent blood loss on the heparinised extracorporeal circuit. 20,000 units of heparin were given i.v. and allowed to circulate. The infrarenal aorta was cannulated with a 20 gauge cannula (Bard), and connected to a closed system containing cold Eurocollins solution (Baxter, Soltran). The portal vein was cannulated with a 24 gauge cannula (Bard) in a similar manner and perfusion with cold Eurocollins solution via the portal vein and aorta was commenced via gravity as the suprahepatic inferior vena cava (IVC) was divided in the pericardium.

After 2 liters of cold Eurocollins solution had perfused through the liver, the liver was removed by excising a cuff of diaphragm around the suprahepatic IVC, dividing the hepatic artery at the celiac axis, the infrahepatic IVC at the level of the renal veins, and the portal vein at the level of the splenic vein. Whilst continuing portal perfusion, the liver was removed from the animal and placed into a bowl at ice temperature. The diaphragmatic remnant was overseen with running 3.0 prolene to secure haemostasis. The suprahepatic IVC was cannulated with a 28 gauge cannula (Bard) with its orifice positioned at the level of the hepatic veins. The inferior vena cava was cannulated with a 6 Fr pressure monitoring cannula (Portex) as was the portal vein via a tributary. The hepatic artery was cannulated with a 10 Fr. cannula (Jostra). Arterial pressures were measured directly from the arterial limb of the circuit. Continuous pressure monitoring was achieved using a transducer (Viggo-Spectramed, Haemodynamic Monitoring Set) and a digital monitor (Datex, AS/3). The bile duct was cannulated with a 14 gauge silastic T-tube with the open end of the T-tube placed into a collection device to monitor bile output.

Perfusion Circuit

While backbench preparation of the liver was performed, the perfusion apparatus (see FIG. 1) was assembled and primed with 1,500 cc of donor pig blood. The perfusion circuit consisted of an oxygenator (Jostra M15 Pediatric Membrane Oxygenator), a centrifugal pump (Medtronic BP50 Centrifugal Pump), a reservoir (Jostra 800 ml soft shelled reservoir), tubing (Medtronic, PVC, ¼ and 3/16 inch internal diameter (ID) with Medtronic Polycarbonate connectors), a gate clamp, pressure transducers (Baxter Triple Pressure Transducers) and flow probes (2 Medtronic DP 38P). The oxygenator was attached to a heat exchanger to maintain the temperature of the blood at 39° C. (normal temperature for a pig).

During priming of the circuit the pH, $paCO_2$ and $Ca^{2+}$ were adjusted to bring them within the normal physiologic range. In general the perfusion circuit was supplemented with 9.2 mmol $CaCl_2$, 20 mmol sodium bicarbonate and 7,000 units of heparin. Once the blood within the circuit was optimized, a sample was then obtained for full blood count, electrolytes, urea, creatinine, liver function tests (LFT), total bilirubin, and plasma was collected and stored in liquid nitrogen for further analysis.

Prior to connection of the liver to the perfusion circuit, the Eurocollins solution was flushed from the portal circulation using 1 liter of colloidal infusion solution (Behring, Haemaccel) This also allowed complete exclusion of air from the liver and cannulae. The liver was placed in an intestinal bag and then suspended in saline in a sterile perfusion chamber. Two soft plastic tubes were placed at the most dependent part of the intestinal bag. These tubes were then connected to the reservoir via an Imed pump (Imed, Gemini PC-4) to recirculate any ascites produced. The liver was connected to the primed perfusion apparatus avoiding any entrapment of air (FIG. 1).

Perfusion was run at a rate of 1-2 liters/min (total) with 100-400 ml/min via the hepatic artery. Artery pressure was maintained at 80-100 (mean) mmHg and IVC pressure 0-3 mmHg. IVC and arterial pressures were adjusted by pump speed and portal flow by means of the height of the reservoir.

Liver Perfusion

After commencement of perfusion, arterial and venous blood samples were obtained at 1 min, 5 min, 10 min, 15 min, 30 min, 1 hour, 2 hour, 4 hour, and then every 4 hours until the end of perfusion. Blood samples were analysed immediately by blood gas analysis (CIBA Corning, 288 Blood Gas System). Oxygen flow and air flow to the oxygenator were adjusted to maintain $paO_2$ between 14-20 kPa and $paCO_2$ between 3.5-6 kPa.

Blood samples were later analysed for full blood count, electrolytes, urea, creatinine, LFTs and total bilirubin. Plasma was stored in liquid nitrogen for later analysis of complement and coagulation pathway components.

Oxygen consumption was calculated using the Fick principle by means of the following equation:

$$O_2 \text{ Content} = 1.39([\text{Hgb}] \text{ in g/dl})(O_2 \text{ sat as \%}) + 0.0031 (pO_2)$$

Each gram of haemoglobin is capable of carrying 1.39 ml of $O_2$ and the amount of $O_2$ dissolved is a linear function of the $PO_2$ (0.0031 ml/dl blood/mm Hg $PO_2$). Establishing the oxygen consumption of the liver is complicated by the fact that the liver has a portal blood supply. Knowledge of the $O_2$ content of the hepatic artery, the portal vein and the hepatic vein is therefore required. In this isolated liver system, the $PaO_2$ of the portal vein and the hepatic artery are the same and therefore the oxygen consumption of the liver can be calculated from:

$$O_2 \text{ consumption} = (\text{Hepatic artery } PO_2 - \text{IVC } PO_2)(\text{Total Flow})$$

Immediately prior to perfusion of the liver with blood, a prostacyclin (Glaxo Wellcome, Flolan) infusion was commenced at 4 mg/hr; in addition, heparin was infused at 500 U/hr and adjusted to maintain an ACT >300 sec. Once perfusion of the liver had commenced, parenteral nutrition was provided. A mixture containing 500 ml of standard total parenteral nutrition solution (Kabi Pharmacia), 50 ml of 10% lipid emulsion (Clintec, IVELIP), 10 ml of trace elements (Pharmacia & Upjohn, Additrace), 1 vial of multivitamins (Clintec, Cernevit), and 72 units of insulin (Novo Nordisk Pharmaceuticals, Ltd., Human Actrapid) was infused at 7 ml/hr throughout the 72 hour perfusion. Additional glucose or insulin was given to maintain glucose within a range of 4-10 mmol/l as determined by blood glucose stick analysis (Boehringer-Mannheim, Accutrend machine and BM-Accutest sticks). At the beginning of perfusion and every 24 hours thereafter 1 g of cefotaxime (Roussel, Claforan) was added to the circuit.

Liver perfusion was electively discontinued at 72 hours and samples from the liver sent for histological evaluation. Random samples were cut from the liver and both frozen for immunohistochemical evaluation and fixed in formalin for hematoxylin and eosin staining.

Sample Analysis

Serum samples from rig serums were analysed for complement production by CH50 analysis (Harrison R. Complement Technology. In: Weir D. M., Herzenberg L. A., Blackwell C., eds. Handbook of Experimental Immunology, 4th Edition, Oxford: Blackwell Scientific Publications, 1986: 39.1-39.49). Briefly, sheep red blood cells (SRBC) were washed three times in complement fixation diluent (ICN Biomedicals. Inc.), diluted to 10%, and coated with antibody SO-16 for 30 minutes on ice. 25 µl of a 1% solution of SO-16-coated SRBC were added to each well of a 96 well microtitre plate. Serum samples from varying time points during liver perfusion were examined starting with a 1:10 dilution and serially diluted 1:4 in triplicate across the microtitre plate. CH50 values were calculated as described by Harrison (Harrison R. Complement Technology. In: Weir D. M., Herzenberg L. A., Blackwell C., eds. Handbook of Experimental Immunology, 4th Edition, Oxford: Blackwell Scientific Publications, 1986: 39.1-39.49). There was variability in CH50 values in the priming blood (porcine blood prior to perfusion through liver) between experiments but consistent values within experiments; therefore, all values are expressed as percentage of prime.

Factor V levels were measured using an Organon Teknika MD180-machine and consumables from Organon for a PT based factor V assay (to abrogate the effects of heparin anti-coagulation). Prothrombin time was measured using the same technique. Electrolytes, LFTs, total bilirubin, creatinine, and urea were measured using standard clinical methods. Full blood counts including hemoglobin, haematocrit, white blood cell count, and platelet counts were obtained using a Coulter counter (T660) adjusted for measurement of porcine blood.

Results

In five experiments, each lasting 72 hours, the mean total hepatic flow was 1.99 l/min (s.d 0.21) at a mean IVC pressure of 2.06 mmHg (s.d. 3.0) (FIG. 2A). The mean portal flow was 1.75 l/min (s.d. 0.21) at a mean pressure of 7.22 mm/Hg (s.d. 2.3) (FIG. 2B). The mean arterial flow was 0.24 l/min (s.d. 0.18) at a mean pressure of 90.3 mm/Hg (s.d. 9.5) (FIG. 252C).

Metabolic function was assessed by measuring pH, $HCO_3-$, $K^+$, base excess and oxygen consumption. Monitoring of pH, $HCO_3-$ and base excess demonstrated essentially normal acid base balance throughout the perfusion (FIG. 3A). Similarly $K^+$ remained at physiological levels throughout the duration of perfusion (FIG. 3B).

As indices of hepatic synthetic function urea, complement and factor V levels were assessed and the results are illustrated in FIGS. 4A, 4B and 4C. The mean urea level for the 5 experiments was 2.92 mmol/L (s.d. 0.55) at the start of perfusion and 45.4 mmol/L (s.d. 6.0) by the end. This is in contrast to the creatinine level that increased from 100 mmol/L (s.d 18.32) to 136.8 mmol/L (s.d. 36.22) This implies that the rise in urea is the result of synthesis as opposed to haemoconcentration. There was a progressive rise in complement activity such that by 72 hours this was on average 383.2% of the starting level (s.d. 111.1). In contrast the factor V levels remained relatively constant, starting with a mean level of 408.4% (s.d 125.5) and ending with a similar amount at 72 hours of 343% (s.d 171.5).

Liver damage was assessed by measuring the level of the liver enzymes alanine transferase (ALT) and alkaline phosphatase (Alk. Phos.). At the end of 72 hours of perfusion the ALT level had changed from 62.4 units/L (s.d. 10.1) to 51.4 units/L (s.d 8.9) (FIG. 5A). Alkaline phosphatase levels fell during the period of perfusion from 136.5 units/liter (s.d. 17.0) to 70.2 units/liter (s.d 12.9) at 72 hours. Bilirubin levels remained low but rose during the perfusion, changing from 0.4 mmol/L (s.d. 0.8) to 32 mmol/L (s.d. 28.2) (FIG. 5B). This rise in bilirubin was associated with a reduction in bile flow and the formation of biliary sludge (FIG. 5B). The biliary sludge usually necessitated intermittent irrigation of the biliary tree to allow adequate biliary drainage.

Oxygen consumption demonstrated an initial peak falling to a trough level by 8 hours where it remained for the rest of the perfusion (FIG. 5C). Mean oxygen consumption at 1 minute for the 5 experiments was 36.2 ml/min (s.d. 3.37) and by 8 hours this was 9.6 ml/min (s.d. 4.06).

In all five experiments there was good preservation of the liver with no overall architectural change. There were a few areas of pericentral necrosis seen in two livers but in general appearances were indicative of excellent viability. Three livers showed areas of mild septal haemorrhage. Four livers showed signs of edema, three moderate and one severe. Sinusoidal congestion was present in all specimens examined involving 5-100 of lobules in two cases, 20-25% of lobules in two cases and 40% of lobules in the remaining liver. Central vein dilation was present in all but one liver involving 25-50% of central veins. Kupffer cell hyperplasia was present in all livers examined. Inspissated bile was present in bile ducts in four out of five livers. Two livers had mononuclear cell infiltrates diffusely within the fibrous septa while the remaining three livers did not demonstrate this.

Discussion

The technique employed for extracorporeal liver perfusion in accordance with the present invention was able to maintain good function and structure for at least 72 hours in the isolated perfused organ. Isolated liver perfusion has not previously been described for periods longer than 24 hours (Neuhaus et al., Int. J. Artif. Organs, 1993; 16: 729-739). Previous investigators usually terminated perfusion as a result of progressive acidosis, hyperkalaemia and rising portal pressures. For this reason the invention represents a significant advance in liver perfusion.

Previous investigators of large animal isolated liver perfusion have asserted that they have maintained physiologic haemodynamic parameters. However, the present inventors have found that if the pump were controlled to maintain physiologic arterial, portal and IVC pressures, blood flow was not maintained at physiologic levels. Total hepatic flow was greater and the ratio of portal venous flow to hepatic arterial flow was higher (7:1) than that described in vivo (3:1). The increase in blood flow was via the portal vein. A review of the literature provides no convincing evidence that any previous investigator has synchronously maintained normal hepatic flows and pressures. The inventors, work shows that portal pressure is autoregulated and influenced by IVC pressure.

Of note is the ability of the isolated perfused liver to maintain the acid base balance and potassium level in this circuit. This is at variance with the experience of others (Mets et al., Journal of Hepatology 1993; 17: 3-9; Adham et al., Transpl. Int., 1997; 10: 299-311) and may be related to a number of factors including the maintenance of liver microstructure and also the provision of metabolic substrate. Other investigators have found it necessary to incorporate a dialysis membrane in the circuit to prevent the development of acidosis and hyperkalaemia (Schon et al., Transplantation Proceedings 1993; 25: 3239-3243). As restoration of normal pH and potassium maintenance is a clinical hallmark of good function in a newly transplanted liver this provides further evidence of the excellent function of the livers perfused in accordance with the present invention.

Although oxygen consumption might reasonably be assumed to be a measure of hepatocyte function, this fell consistently during the course of perfusion. This is in contrast to other markers of liver function, particularly synthetic activity. However, the initial values obtained for oxygen consumption correlate well with figures derived in vivo by a number of authors (Mathisen and Omland, Scand J of Gastroent 25: 1265-1273, 1990; Rasmussen et al., Eur J Surg 159: 201-7, 1993; Lindberg and Clowes, Jr., J Surg Research 31: 156-64, 1981; Imamura, Surgery, Gynaecology and Obstetrics 141: 27, 1975; Tygstrup et al., Scan J Gastroent Suppl 9: 131-138, 1971. and p 139-148; Mets et al., Journal of Hepatology 1993; 17: 3-9). In this experimental situation the liver is denervated and not exposed to the normal hormonal stimuli to which it is subjected in vivo. It is possible that the liver is relatively inactive in this situation which may account for the relatively low level of oxygen consumption observed. In support of this hypothesis, a transient sharp rise in oxygen consumption was consistently observed when intermittent insulin boluses were added to the circuit.

Bile production in this extracorporeal perfusion system peaked at 12.8 ml/hour approximately half of that observed in vivo. Bile production decreased with time and inspissated bile was seen macroscopically in all livers and histologically in four out of five experiments. This may reflect consumption of substrate (including bile salts), loss of hormonal or neural stimuli and/or inadequate biliary drainage with accumulation of biliary sludge (although alkaline phosphatase did not rise) Serum bilirubin levels remained low for the first 24 hours of perfusion and started to rise concomitantly with the fall in bile production.

Enzymatic markers of hepatocyte damage did not rise during perfusion. Using the same assay, these enzymes are substantially elevated in a porcine model of acute hepatic failure used by our group. This suggests that there is good preservation of hepatocyte viability in spite of biliary obstruction and rising bilirubin.

Further evidence of hepatocellular function was provided by the demonstration of protein synthesis. FIGS. 4A, 4B and 4C show evidence of continued synthetic function throughout the 72 hour perfusion. It is of interest to note that complement production was apparently not regulated by a feedback mechanism in the liver, but appeared to continue at a constant rate accumulating in the plasma of the isolated circuit (FIG. 4B). The mechanisms that regulate complement production by the liver remain poorly understood. In contrast Factor V activity remained at a relatively constant level throughout the 72 hour perfusion period. The significance of the different patterns seen in the balance of synthesis and consumption for these two proteins is unclear.

While 3 of 5 livers showed no necrosis, the few areas of necrosis seen were pericentral in location suggesting ischaemic damage, but this was insufficient to cause a rise in ALT or alkaline phosphatase levels. There was consistent evidence of edema, sinusoidal congestion and central vein dilation. These findings may suggest inadequate venous drainage despite physiological IVC pressures.

After early perfusion failure in preliminary experiments, prostacyclin was used routinely. Thus, while the role of prostacyclin has not been rigorously investigated, we believe its use is desirable in liver perfusion. It is unclear whether it is the vasodilator or anti-platelet activity of prostacyclin that provides the beneficial effects in this situation. However, an agent which mimics one or other or both of these activities may be useful in place of prostacyclin.

EXAMPLE 2

Extra-Corporeal Perfusion OF hDAF Transgenic Pig Livers with Human Blood

The perfusion apparatus and technique employed in Example 1 was used to perfuse porcine livers transgenic for the complement regulator protein, human decay accelerating factor (hDAF), when perfused with fresh, whole, human blood. Three experimental groups were studied: alloperfusions (normal pig livers perfused with pig blood) and xenoperfusions of both unmodified and hDAF transgenic pig livers with human blood.

Alloperfusion resulted in the maintenance of good function and histological structure for periods of at least 72 hours. Xenoperfusions were also carried out for periods of up to 72 hours but, unlike alloperfusions, were marked by a progressive decrease in haematocrit of the circulating blood. Histological examination demonstrated patchy necrosis but most lobules were normal. Effective liver function was demonstrated in both normal and transgenic liver perfusions.

Three groups were studied with 5 experiments in each group.

Group. A. Alloperfusions, Normal porcine livers perfused with pig blood.

Group B: Xenoperfusions, Normal (non-transgenic) porcine livers perfused with human blood Group C: Transgenic xenoperfusions, Transgenic porcine livers perfused with human blood.

In each group the same experimental protocol was applied.

Donor pig livers were prepared as in Example 1. Human blood was obtained from volunteer donors and used within 4 hours of donation.

The perfusion circuit (FIG. 1) was employed as in Example 1 Perfusion was stopped electively at 72 hours or earlier if liver failure was deemed to have occurred—pH<7.0, rapidly rising potassium or increasing portal pressure. At this time multiple samples were taken from the liver both for immunohistochemical evaluation and hematoxylin and eosin staining.

Serum samples were analysed for complement production by CH50 analysis. Factor V was measured using an assay based upon prothrombin time (Organon Teknika MD180). Prothrombin time was also measured. Electrolytes, biochemical liver function tests, creatinine, and urea were measured using standard clinical methods. Full blood count analysis was performed using a Coulter counter (T660) adjusted for measurement of porcine blood.

Results

The flow and pressure data for the three groups are shown in Table 1 below.

These results have been analysed using a 2-tailed T test (Table 2). No significant difference was found for either portal or total flow between transgenic and non-transgenic xenoperfusions. However, alloperfusions showed significantly higher total and portal flows than xenoperfusions ($p=0.05$, $p=0.025$). With respect to both arterial flow and IVC pressure, significant differences were seen between control and transgenic xenoperfusions ($p=0.05$, $p=0.05$). No significant differences in arterial flow could be shown between any of the experimental groups. Whilst no significant difference was seen in portal pressure between alloperfusions and transgenic xenoperfusions, significant differences were demonstrated between non-transgenic xenoperfusions and both alloperfusions and transgenic xenoperfusions ($p=0.01$, $p=0.01$).

As a measure of metabolic function the acid-base balance of the circuit was assessed by pH, bicarbonate and base excess. Base excess reflects only the metabolic effect of the perfused liver in isolation. In all three groups an initial profound metabolic acidosis was progressively corrected. The transgenic xenoperfusions behaved similarly to the alloperfusions (no significant difference), whereas acid-base was less effectively corrected in the non-transgenic xenoperfusions ($p=0.005$) (FIG. 6A). As a further measure of hepatic metabolic function, potassium levels were measured. Both xenoperfusion groups showed significantly higher potassium levels than alloperfusions ($p=0.01$, $p=0.05$), most marked after 48 hours of perfusion (FIG. 6B. Oxygen consumption (ml/hour) for the three groups is outlined in Table 3 below.

A consistent pattern in oxygen consumption was seen in both xenoperfusion groups with an initial fall followed by a terminal rise; the latter was not seen in alloperfusions.

Figure 7:
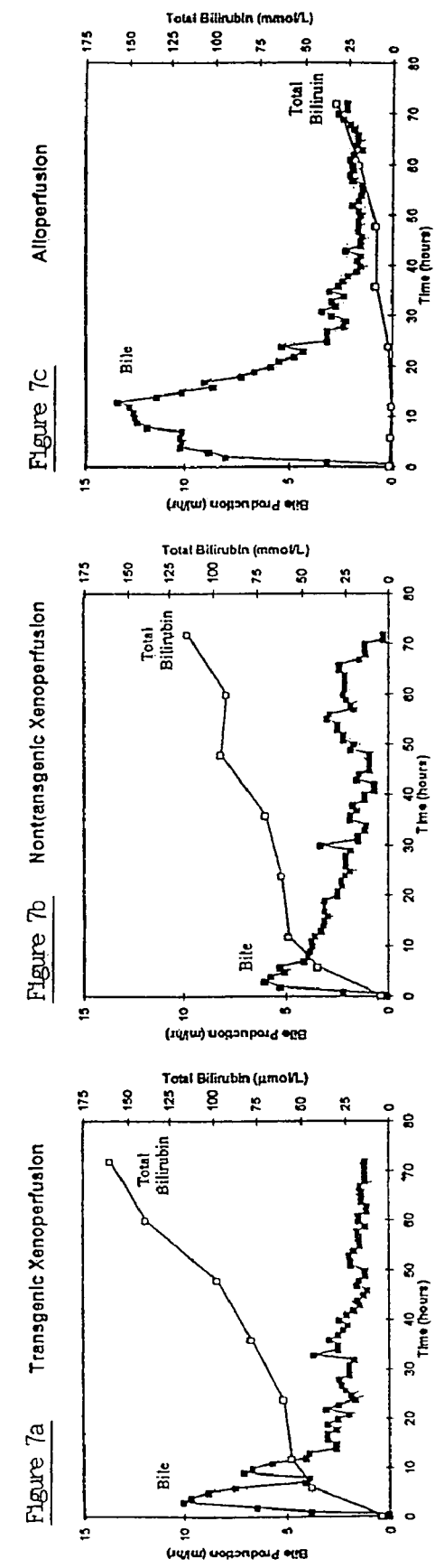
FIG. 7 shows bile output measured as ml bile produced per hour and total bilirubin expressed in μmol/L (normal human range up to 17 μmol/L.

Bile production (ml/hour) in the three groups is outlined in FIG. 7.

Whilst there was no significant difference in bile production between the xenoperfusion groups, these produced significantly less bile than alloperfusions ($p=0.025$, 0.05). Total bilirubin levels rose progressively in all three groups. Whilst there was no significant difference between xenoperfusions (terminating at 138.8 mmol/L and 160.5 mmol/L), the level in the alloperfusion group was significantly lower (32 mmol/L) ($p=0.0005$, $p=0.0005$) (FIG. 7).

Whereas the white cell counts in both xenoperfusion groups fell to less than $1.0 \times 10^9$/L within 1 hour, white cell counts of $>1.0 \times 10^9$/L were maintained until 52 hours during alloperfusions (not significant) (FIG. 8B). Platelet counts also dropped during both normal and transgenic xenoperfusions, the only significant difference was between non-transgenic xenoperfusions and alloperfusions ($p=0.005$) (FIG. 8A) There was a progressive reduction in haematocrit in all three groups (FIG. 8C). By 72 hours the terminal haematocrit was 46.9%, 1.9% and 0.3% (alloperfusion, non-transgenic, transgenic). Statistically significant differences were demonstrated between all 3 groups (FIG. 8C).

Transgenic livers synthesised significantly more urea than non-transgenic livers ($p=0.01$) (FIG. 9A). The alloperfusion group synthesised significantly less urea than either xenoperfusion group ($p=0.025$, $p=0.0005$). Demonstrating that this was due to synthesis rather than haemoconcentration, creatinine levels demonstrated at most a 1.7 fold concentration over the 72 hour perfusion.

Measured factor V activity in the alloperfusion was approximately 400%; this was maintained throughout the period of perfusion (FIG. 9B). Both xenoperfusion groups demonstrated initial factor V levels of 100% increasing with time to 200w and 324% respectively. There was no significant difference between the xenoperfusion groups; it is not appropriate to compare the alloperfusion and xenoperfusion groups because the initial values were so different and the analysis requires calculation of the area under the curve.

Complement activity is demonstrated in FIG. 9C. All three groups show an initial decrease in complement activity followed by an increase. At 72 hours, the alloperfusion group had a complement activity of 382% (relative to the starting level), non-transgenic xenoperfusions 27% and transgenic xenoperfusions 88%. Statistically significant difference was demonstrated between all groups.

Terminal alanine transaminase levels of 51.4 units/L, 115 units/L and 128 units/L were measured in the alloperfusion, non-transgenic and transgenic groups respectively. Whilst there was no statistically significant difference between the xenoperfusion groups, the alloperfusion group demonstrated significantly lower levels than either xenoperfusion group ($p=0.0005$, 0.005). In all three groups the alkaline phosphatase levels decreased with time with transgenic xenoperfusions showing significantly lower levels non-transgenic (39 units/liter versus 28 units/liter at 72 hours) ($p=0.005$). It is not appropriate to compare alloperfusion with xenoperfusions because the normal alkaline phosphatase level in porcine blood is twice that of human blood.

In the transgenic group necrosis was seen in all livers. In three livers necrosis was patchy involving 10-30% of the livers, in one the necrosis was subcapsular involving 5% of the liver and in one there was diffuse necrosis involving 80% of the liver. No consistent pattern of liver damage could be determined. Because of the significant necrosis in one of the livers, further histologic analysis was not possible. In the remaining four livers, sinusoidal dilatation and was seen in 3, central dilatation in 2, and septal edema in one. Inspissated bile was present in the intralobular bile ducts of all four livers.

Endothelitis was present in one of the four livers. Haemorrhage was present in the lymphatics of one of the livers. Kupffer cell hypertrophy was present in all livers with significant Perl's staining of intracellular iron.

In the non-transgenic group haemorrhage was seen in all livers, but necrosis outside of the haemorrhagic areas was not apparent. The haemorrhage involved the hepatic parenchyma in all livers, involving septal and sinusoidal haemorrhage in four livers while being more prominent in the subcapsular region in one liver. All livers demonstrated sinusoidal dilatation with retained red cells within sinusoids, 2 livers had evidence of central vein dilatation, and four of five livers had septal edema. None of the livers had inspissated bile. One liver had mild endothelitis. There was very mild Kupffer cell hypertrophy and minimal Perl'staining of intracellular iron in 4 of five livers.

Overall, sinusoidal and connective tissue haemorrhage was seen only in the non-transgenic livers. In these non-transgenic livers there was relatively little parenchymal necrosis or iron accumulation. In contrast, the transgenic group showed more extensive coagulative necrosis than in the non-transgenic or alloperfusion groups and intra-Kupffer cell iron was more prominent. Unfortunately, immunohistochemical analysis of frozen sections from these experiments was not interpretable.

Discussion

The experiments described in Example 2 demonstrate that the invention is effective not only in alloperfusion (as described in Example 1) but also in more demanding xenoperfusion.

These experiments provide clear evidence that porcine livers function when perfused with human blood. It has long been recognised that the liver is relatively protected from damage from preformed antibodies (Collins et al., Transplantation 1994; 58: 1162-1171) hyperacute rejection has rarely been reported and liver transplantation is frequently performed in the presence of a positive lymphocyte cross-match (Hathaway et al., Transplantation 1997; 64: 54-59; Goggins et al., Transplantation 1996; 62: 1794-1798).

Any use of the term hyperacute rejection requires definition; the histological appearances of hyperacute rejection overlap with those of acute vascular rejection (Platt, ASAIO. J. 1992; 38: 8-16). Thus the diagnosis requires not only characteristic histological features (microthrombosis and haemorrhage) but also the absence of organ function at any time.

Hyperacute rejection was not observed in either transgenic or non-transgenic xenoperfusions in this study. This protection from hyperacute rejection may be a function of the liver itself or of the non-physiological nature of the perfusion circuit, particularly the limited volume of blood (and immunological effector components) or the use of heparin. In this context it is of note that hyperacute rejection has been demonstrated in a heparinised ex vivo xenoperfusion model of the heart (Dunning et al., Eur. J. Cardiothorac. Surg. 1994; 8: 204-206).

In a recent study of ex vivo porcine liver xenoperfusions, deposition of human antibodies and complement components in association with tissue damage were demonstrated by four hours (Pascher et al., Transplantation 1997; 64: 384-391) Thus, whilst the liver is protected from hyperacute rejection, it is still vulnerable to antibody mediated damage. Previous attempts at porcine ex vivo liver perfusion in the clinical setting have resulted in failure that was presumed to be immunologically mediated (Abouna et al., Br. J. Surg. 1968; 55: 862). These perfusions were characterised by progressively rising portal pressure and subsequent perfusion failure. By contrast, in the present study, in both transgenic and non-transgenic xenoperfusions portal perfusion pressures remained within physiological limits. Interpretation of the histology in this study has been restricted by the design of the experiment; samples were only obtained at the termination of the experiment at which time severe ischaemic liver damage had occurred secondary to the fall in haematocrit.

Despite the absence of hyperacute rejection in both groups, it is clear that the introduction of the hDAF transgene does have some important consequences. There are significant differences between the transgenic and non-transgenic perfused livers in respect of portal and IVC pressures, arterial flow, acid-base maintenance and synthesis of both urea and complement. It is hypothesised, therefore, that, although insufficient to destroy the liver, the immediate complement mediated immune response did initiate enough damage to impair the microcirculation and impair metabolic and synthetic function. It can be argued that this effect, in a closed circuit with limited immunological effector mechanisms, is likely to be an under-estimate of the effect which would be incurred in treatment of a patient in which the liver would be exposed to a much greater circulating volume.

Whereas in respect of those parameters discussed above the transgenic livers behaved similarly to the alloperfused livers, analysis of other parameters demonstrated similar behaviour between both xenoperfused groups and significant differences from the alloperfused group. These include some haemodynamic parameters, total and portal flows, potassium levels, bile production and bilirubin levels, transaminase levels and terminal oxygen consumption. Analysis of bile production and bilirubin levels may be complicated by the considerable differences in red cell breakdown and suspected complications of biliary sludge formation. Also, depletion of bile salts may be a further factor in bile production. Similarly, potassium levels may reflect differences in red cell breakdown. The performance of both xenoperfused groups deteriorates towards the end of the 72 hour experiments; this is demonstrated by the terminal oxygen consumption figures. It is likely that this is, at least in part, a reflection of the decreasing haematocrit leading to loss of oxygen carrying capacity of the blood. This correlates with the higher level of transaminase enzymes in these experiments that might, therefore, be a manifestation of ischaemia.

An unexpected finding of this study was a progressive reduction in haematocrit, noticeable in the alloperfusions, but very marked in the non-transgenic group and significantly worse in the transgenic group. While mechanical damage is caused by the pump and circuit (haemolysis was noted to occur when blood was circulated in the perfusion apparatus without a liver), this accounts for a very small proportion of the loss of red blood cells. Most of the haematocrit reduction in the alloperfusion group can be accounted for by dilution, the combination of repeated blood sampling and constant infusion of other fluids (prostacyclin, nutrition). Estimation of terminal haematocrit as a percentage of prime, correcting for the dilutional effects, results in figures of: perfusion apparatus alone (93.3%), alloperfusion (85.3%), non-transgenic xenoperfusion (3.3%), and transgenic xenoperfusion (0.5%). The significant difference between the alloperfusion and both xenoperfusion groups suggests an important effect of immunological aetiology. Several possible mechanisms have been hypothesised. These include the effect of porcine anti-human antibodies eluted from or produced by the liver. These might be effective by opsonisation (leading to removal by Kupffer cells) or complement (human or porcine) mediated lysis. Porcine complement might be activated directly via the alternative pathway. Finally, the reticuloendothelial system in the liver might extract red blood cells either by recognition of species-specific differences or pump related erythrocyte damage. The significant difference in terminal haematocrits between the transgenic and non-transgenic groups is not explained but may be related to improved microcirculation in the transgenic livers.

The effect is likely to be particularly marked in the artificial situation of the isolated perfusion circuit and, indeed, calculation based upon the rate of red cell loss suggests that blood transfusion at the rate of less than one unit per day would be required if this system were used in extra-corporeal support of a patient.

Whilst initial interpretation of the data from these experiments would suggest that the xenoperfused livers function significantly less well than alloperfused livers, closer scrutiny suggests that this may be misleading. It is notable that liver function, as assessed by those parameters not directly affected by red cell breakdown, is maintained to the same level in xenoperfusions (particularly transgenic) as in alloperfusions. In particular this is illustrated by the synthesis of Factor V and haemodynamic parameters. The measurement of potassium, hydrogen ions, bilirubin and urea are directly affected by red cell breakdown. Also, complement levels represent a balance between production and consumption; a higher level of consumption is inevitable in xenoperfusions.

It is clear that the perfused livers provide metabolic function and are capable of normalisation of potassium and acid-base balance; these are cardinal features of good liver function following liver transplantation. The synthetic functions of the liver, although potentially of some benefit, may be problematical. The synthesis of high levels of porcine complement may lead to damage of human tissues that are not protected by appropriate species specific complement regulators. However preliminary data from recent experiments suggest that serum from xenoperfusions does not cause lysis of fresh human red cells in vitro. There is potential incompatibility between porcine proteins and the human environment (Lawson et al., Transplant. Proc. 1997; 29: 884-885; Reverdiau-Moalic et al., Transplant. Proc. 1996; 28: 643-644). The activity of Factor V in normal pig serum is maintained at a level four times that of human serum when measured using a human functional assay. It is not known whether this will lead to coagulation abnormalities in the clinical situation. Finally, there is some evidence that an antibody response may be induced to porcine proteins. This may, under certain circumstances, lead to an autoimmune phenomenon (Ortel et al., Am. J. Hematol. 1994; 45: 128-135).

These experiments demonstrate that perfusion of a porcine liver with human blood is compatible, at least in the medium term, with function comparable with that obtained using porcine blood. There is some clear evidence of a beneficial effect of the introduction of the hDAF transgene.

EXAMPLE 3

Extra-Corporeal Support of Pigs in Acute Liver Failure

Acute liver failure was induced in eight non-transgenic pigs by pre-treatment with oral phenobarbitone for 3 days, instillation of intra-gastric carbon tetrachloride and ligation of the hepatic artery.

Four pigs were allowed to recover from the anaesthetic. Parameters of liver function (urea and electrolytes, liver function test, coagulation profile, arterial blood gases and serum ammonia) were monitored as acute liver failure developed. Liver failure was confirmed from post-mortem liver biopsies.

Four pigs remained under general anaesthesia for 12-15 hours after ligation of the hepatic artery before being connected to the extracorporeal liver perfusion circuit described above. Liver function, cardiovascular status and arterial blood gases were monitored. In all four experiments the duration of perfusion was limited by technical issues. Post-mortem samples were taken to assess the degree of liver damage; samples of lung and kidney were taken to look for evidence of embolic phenomena secondary to perfusion.

The four pigs not treated with extracorporeal liver perfusion survived for 15.5±5.2 hours. Acute liver failure developed in all four pigs: there were massive increases in liver enzymes and significantly increased ammonia levels. Histology demonstrated confluent hepatocellular necrosis with almost no viable liver cells remaining.

The four pigs treated with extracorporeal liver support survived for 31, 33, 35 and 52 hours (37.8±9.6 hours), significantly longer than the untreated pigs (p<0.005). The oxygenator failed after 24 hours in the first two perfusions. In the remaining two perfusions, for which a different type of oxygenator was used, ventilatory failure secondary to mucus plugging in the pigs necessitated discontinuation of liver perfusion after 22 and 37 hours of perfusion.

Immediately before starting liver perfusion the pigs were moribund, with extreme tachycardia (160±0 beats per minute), hypotension (80/42.5±0/3.5 mmHg) and metabolic acidosis (mean pH 7.20±0.12). After one hour of extracorporeal liver perfusion, the acidosis was reversed, returning to a physiological range (pH 7.36±0.08), and the tachycardia improved (127.5±3.5 beats per minute).

Figure 10:
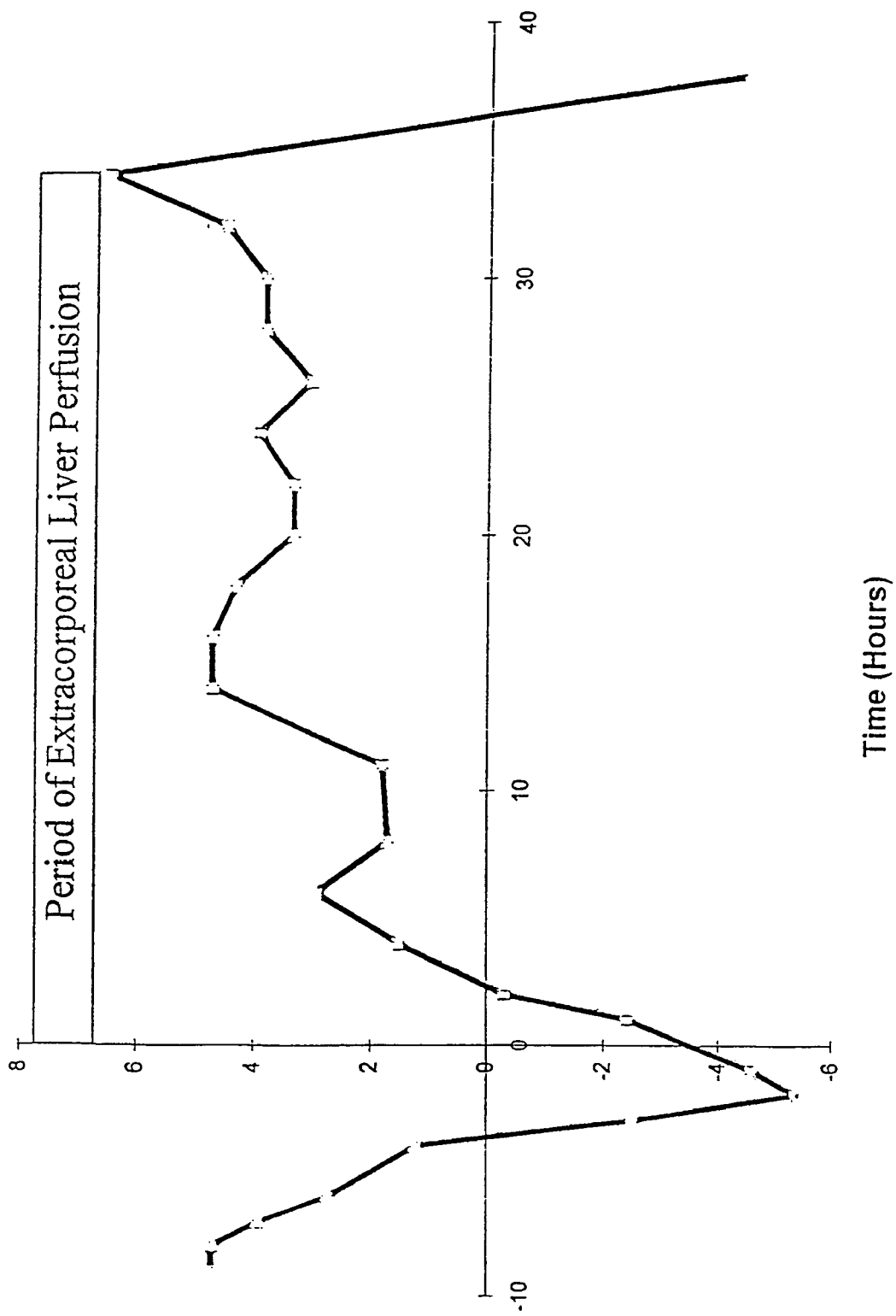
FIG. 10 shows base excess during liver support and rescue, indicating a rapid declining after perfusion ceased.

After stopping perfusion, both pigs deteriorated rapidly and died within one hour (FIG. 10).

TABLE 1

Hemodynamic Data

| | Alloperfusion (s.d.) | Nontransgenic (s.d.) | Transgenic (s.d.) |
|---|---|---|---|
| Total Flow (L/min) | 2.01 (0.12) | 1.80 (0.27) | 1.88 (0.20) |
| Portal Flow (L/min) | 1.75 (0.18) | 1.60 (0.24) | 1.58 (0.22) |
| Hepatic Artery Flow (L/min) | 0.237 (0.054) | 0.229 (0.094) | 0.296 (0.065) |
| IVC Pressure (mm Hg) | 2.20 (1.04) | 2.91 (0.86) | 1.64 (0.80) |
| Portal Pressure (mm Hg) | 7.08 (1.2) | 11.4 (2.9) | 7.23 (2.1) |
| Arterial Pressure (mm Hg) | 90.3 (2.6) | 87.0 (4.1) | 89.4 (3.8) |

TABLE 2

Hemodynamic Data Statistical Significance

| | Alloperfusion vs. Nontransgenic | Alloperfusion vs. Transgenic | Nontransgenic vs. Transgenic |
|---|---|---|---|
| Total Flow | 0.05 | 0.05 | NS |
| Portal Flow | 0.025 | 0.025 | NS |
| Arterial Flow | NS | NS | 0.05 |
| IVC Pressure | NS | NS | 0.05 |
| Arterial Pressure | NS | NS | NS |
| Portal Pressure | 0.01 | NS | 0.01 |

TABLE 3

| | Oxygen Consumption (ml O₂/min) | | |
| --- | --- | --- | --- |
| | Alloperfusion | Nontransgenic | Transgenic |
| 5 Minutes | 19.1 | 35.7 | 42.5 |
| Trough Level | 7.01 | 10.8 | 18.8 |
| Terminal Level | 7.01 | 38.6 | 64.6 |

The invention claimed is:

1. A method of perfusing a mammalian organ extracorporeally, the organ being other than a beating heart, said method comprising pumping blood to an input artery of the extracorporeal organ and to a pressure relieving reservoir whereby physiological pressure and variable flow rate in the artery of the organ are maintained by variable flow into the reservoir, and pumping venous outflow from the organ such that physiological pressure in the output vein of the organ is maintained, said method allowing the organ to autoregulate blood flow through itself to achieve physiological arterial flow.

2. The method of claim 1 wherein said organ is selected from the group consisting of a liver, a kidney, a pancreas and a small bowel.

3. The method according to claim 2 in which the organ is a liver, the method further comprising maintaining a physiological portal vein flow rate and pumping venous outflow from the liver to maintain physiological pressure in the vena cava of the liver, while allowing the liver to autoregulate portal vein pressure.

4. The method according to claim 3 further comprising collecting fluid that leaks from the liver and recirculating the collected fluid directly or indirectly back to the liver.

5. A method of maintaining viability of a mammalian organ, wherein the organ is perfused in accordance with the method of any one of claims 1 to 4.

6. The method according to claim 5 comprising maintaining viability of the organ for at least about 72 hours.

7. The method according to any one of claims 1 or 2 wherein the organ is a liver.

8. The method according to claim 7 wherein the liver is porcine.

9. The method according to claim 8 wherein the porcine liver is genetically engineered to express human protein.

10. The method according to claim 7 wherein the liver is human.

11. A mammalian liver perfusion apparatus comprising
a variable speed outflow pump the input of which is directly in fluid connection with a structure defining an input flow passage to said pump,
said input flow passage being configured to form a direct fluid connection from the vena cava of a mammalian liver when said apparatus is connected to said mammalian liver and operated in a perfusion process,
a structure defining an output flow passage from said pump and forming a direct or indirect fluid connection between said pump and
a bifurcating structure,
said bifurcating structure containing a bifurcation
a first structure defining a first fluid passage downstream of said bifurcation, and
a second structure defining a second fluid passage downstream of said bifurcation,
said first fluid passage being in fluid connection with a reservoir, and
said second fluid passage being configured to form a fluid connection with the hepatic artery of a mammalian liver when said apparatus is connected to said mammalian liver and operated in a perfusion process,
a structure configured to form a flow passage downstream of said reservoir and from said reservoir to the portal vein of a mammalian liver when said apparatus is connected to said mammalian liver and operated in a perfusion process, and
at least one of a heat exchanger and an oxygenator, configured to be in fluid connection between output flow of said vena cava and input flow of said hepatic artery and said portal vein when said apparatus is connected to said mammalian liver and operated in a perfusion process,
said reservoir being configured to maintain physiological pressure in the hepatic artery and physiological flow in the portal vein, when said apparatus is connected to said mammalian liver and operated in a perfusion process, while allowing a said mammalian liver to autoregulate blood flow through the hepatic artery and to autoregulate pressure in the portal vein.

12. The apparatus according to claim 11 wherein said bifurcating structure defines a flow passage from said oxygenator or said heat exchanger to said reservoir and is configured to also form a flow passage to the hepatic artery of said mammalian liver, said bifurcating structure further comprising a variable restriction structure downstream of said bifurcation.

13. The apparatus according to claim 12 further comprising a flow sensor.

14. The apparatus according to claim 13 wherein the reservoir is arranged and constructed and configured to supply blood under force of gravity to the portal vein of said mammalian liver, when said apparatus is connected to said mammalian liver and operated in a perfusion process.

15. The apparatus according to any one of claims 11-14 further comprising
a third structure which is configured to collect fluid which leaks from said mammalian liver, when said apparatus is connected to said mammalian liver and operated in a perfusion process, and
a fourth structure constructed to define a direct or indirect flow passage from said third structure back to said mammalian liver when said apparatus is connected to said mammalian liver and operated in a perfusion process.

16. The apparatus according to any one of claims 11-14 further comprising connections configured to join the apparatus to the circulatory system of a mammal when said apparatus is connected to said mammalian liver and operated in a perfusion process.

17. A method of perfusing a mammalian liver comprising:
connecting the vena cava of the mammalian liver to the inflow passage of the apparatus of any of claims 11-14, connecting the hepatic artery of the mammalian liver to the second fluid passage of the apparatus and connecting the portal vein to the structure configured to form a flow passage from the reservoir to the portal vein of the apparatus, in any order, to provide a fluid circuit of blood flow through the liver,
the method further comprising adjusting the speed of the outflow pump to maintain physiological pressure in the vena cava, adjusting pressure at the bifurcating structure-connected to the hepatic artery to maintain physiological pressure in the hepatic artery and adjusting the flow in the structure defining a flow passage from said reservoir to the portal vein to maintain physiological flow in the portal vein, and allowing the mammalian liver to autoregulate blood flow through the hepatic artery and to autoregulate pressure in the portal vein.

18. The method according to claim 17 wherein the liver is porcine.

19. The method according to claim 18 wherein the porcine liver is genetically engineered to express human protein.

20. The method according to claim 17 wherein the liver is human.

21. A mammalian organ perfusion apparatus comprising
a variable speed outflow pump the input of which is directly in fluid connection with a structure defining an input flow passage to said pump,
said input flow passage being configured to form a direct fluid connection from the output vein of a mammalian organ when said apparatus is connected to said mammalian organ and operated in a perfusion process,
a structure defining an output flow passage from said pump and forming a direct or indirect fluid connection between said pump and
a bifurcating structure,
said bifurcating structure containing a bifurcation
a first structure defining a first fluid passage downstream of said bifurcation, and
a second structure defining a second fluid passage downstream of said bifurcation,
said first fluid passage being in fluid connection with a reservoir, and
said second fluid passage being configured to form a fluid connection with the artery of a mammalian organ when said apparatus is connected to said mammalian organ and operated in a perfusion process,
a structure configured to form a flow passage downstream of said reservoir and from said reservoir to the artery of a mammalian organ when said apparatus is connected to said mammalian organ and operated in a perfusion process, and
at least one of a heat exchanger and an oxygenator, configured to be in fluid connection between output flow of said vein and input flow of said artery when said apparatus is connected to said mammalian organ and operated in a perfusion process,
said reservoir being configured to maintain physiological pressure in the artery and physiological flow in the vein, when said apparatus is connected to said mammalian organ and operated in a perfusion process, while allowing a said mammalian organ to autoregulate blood flow through the artery and to autoregulate pressure in the vein.

22. A method according to claim 17, wherein the blood is citrated.

* * * * *

UNITED STATES PATENT AND TRADEMARK OFFICE
CERTIFICATE OF CORRECTION

| | | |
|---|---|---|
| PATENT NO. | : 7,410,474 B1 | Page 1 of 1 |
| APPLICATION NO. | : 09/958681 | |
| DATED | : August 12, 2008 | |
| INVENTOR(S) | : Friend | |

It is certified that error appears in the above-identified patent and that said Letters Patent is hereby corrected as shown below:

On the Title Page, item (22): delete "PCT Filed: Apr. 12, 2000" and insert therefore --PCT Filed: Apr. 5, 2000--

Signed and Sealed this

Seventeenth Day of April, 2012

David J. Kappos
*Director of the United States Patent and Trademark Office*